US009116146B2

(12) United States Patent
Shen et al.

(10) Patent No.: US 9,116,146 B2
(45) Date of Patent: Aug. 25, 2015

(54) QUANTITATIVE AND SELF-CALIBRATING CHEMICAL ANALYSIS USING PAPER-BASED MICROFLUIDIC SYSTEMS

(75) Inventors: Wei Shen, Victoria (AU); Xu Li, Victoria (AU); Junfei Tian, Melbourne (AU); Gil Garnier, Frankston South (AU)

(73) Assignee: Monash University, Clayton (AU)

( * ) Notice: Subject to any disclaimer, the term of this patent is extended or adjusted under 35 U.S.C. 154(b) by 311 days.

(21) Appl. No.: 13/380,303

(22) PCT Filed: Jun. 30, 2010

(86) PCT No.: PCT/AU2010/000837
§ 371 (c)(1),
(2), (4) Date: Mar. 14, 2012

(87) PCT Pub. No.: WO2011/000047
PCT Pub. Date: Jan. 6, 2011

(65) Prior Publication Data
US 2012/0171702 A1    Jul. 5, 2012

(30) Foreign Application Priority Data
Jun. 30, 2009    (AU) ................................ 2009903024

(51) Int. Cl.
*B01L 3/00*    (2006.01)
*G01N 33/52*    (2006.01)
(Continued)

(52) U.S. Cl.
CPC ............ *G01N 33/52* (2013.01); *B01L 3/50273* (2013.01); *G01N 21/78* (2013.01);
(Continued)

(58) Field of Classification Search
CPC ................ G01N 21/75–21/77; G01N 33/558; G01N 33/543; G01N 33/54306; G01N 33/54353; G01N 33/54386; G01N 33/54393; B01L 2300/0887; B01L 2300/0816; B01L 2300/0825; B01L 2300/0861; B01L 2300/0864; B01L 2300/0867
USPC ................... 422/70; 435/4, 7.1, 970; 436/162
See application file for complete search history.

(56) References Cited

U.S. PATENT DOCUMENTS 3,929,580 A    12/1975 Forgione et al.
2003/0119203 A1*    6/2003 Wei et al. ...................... 436/514
(Continued)

FOREIGN PATENT DOCUMENTS

CN    101076601    11/2007
WO    WO 2006/065900    6/2006
(Continued)

OTHER PUBLICATIONS

Li, et al., "Paper-based Microfluidic Devices by Plasma Treatment", Analytical Chemistry, Dec. 1, 2008, 80(23), 9131-9134.
(Continued)

*Primary Examiner* — Melanie Y Brown
*Assistant Examiner* — Erik B Crawford
(74) *Attorney, Agent, or Firm* — Baker & Hostetler LLP

(57) ABSTRACT

A method of determining the concentration of a test fluid sample using a paper-based microfluidic system having a plurality of hydrophilic testing zones, including: a) depositing said test fluid sample on at least one said testing zone; b) depositing a plurality of standard fluid samples or reactives of differing known concentrations on other said testing zones; c) introducing an indicator solution to each said test zone to thereby react with the deposited fluid sample and result in a color intensity change which is a function of the fluid sample concentration; and d) comparing the differences in color intensity between the test fluid sample and the standard fluid samples or reactives to thereby determine the concentration of said test fluid sample.

7 Claims, 3 Drawing Sheets

(51) Int. Cl.
  *G01N 33/543* (2006.01)
  *G01N 21/93* (2006.01)
  *G01N 21/78* (2006.01)
  *G01N 33/53* (2006.01)
  *G01N 33/558* (2006.01)

(52) U.S. Cl.
  CPC ........... *G01N 21/93* (2013.01); *G01N 33/5302* (2013.01); *G01N 33/543* (2013.01); *G01N 33/54366* (2013.01); *G01N 33/54386* (2013.01); *G01N 33/558* (2013.01); *B01L 2300/0816* (2013.01); *B01L 2300/0864* (2013.01); *B01L 2300/126* (2013.01); *B01L 2400/0406* (2013.01); *Y10T 436/148888* (2015.01); *Y10T 436/173076* (2015.01)

(56) References Cited

U.S. PATENT DOCUMENTS

2006/0000722 A1* 1/2006 Parce et al. ................ 205/777.5
2010/0285490 A1* 11/2010 Dees et al. .................... 435/7.1

FOREIGN PATENT DOCUMENTS

WO  WO 2008/049083 A2  4/2008
WO  WO 2011/000047      1/2011

OTHER PUBLICATIONS

Martinez, et al., "Three-dimensional Microfluidic Devices Fabricated in Layered Paper and Tape", Proceedings of the National Academy of Sciences, Jan. 1, 2008, 105(50), 19606-19611.

Martinez et al., "Patterned paper as a platform for inexpensive, low-volume, portable bioassays", Angew. Chem. Int. Ed., Feb. 2007, 46(8), 1318-1320.

Allen et al., "A Noninstrumented Quantitative Test System and Its Application for Determining Cholesterol Concentration in Whole Blood", Clinical Chemistry, 1990, 36(9), 1591-1597.

Martinez et al., "Simple Telemedicine for Developing Regions: Camera Phones and Paper-Based Microfluidic Devices for Real-Time, Off-Site Diagnosis", Anal. Chem., 2008, 80(10), 3699-3707.

* cited by examiner

QUANTITATIVE AND SELF-CALIBRATING CHEMICAL ANALYSIS USING PAPER-BASED MICROFLUIDIC SYSTEMS

CROSS-REFERENCE TO RELATED APPLICATIONS

This application is the National Stage of International Application No. PCT/AU2010/000837, filed Jun. 30, 2010, which claims the benefit of Australian Application No. 2009903024, filed Jun. 30, 2009, the disclosures of which are incorporated herein by reference in their entireties.

FIELD OF THE INVENTION

The present invention is generally directed at quantitative chemical analysis systems, and in particular to chemical analysis using paper-based microfluidic systems.

BACKGROUND OF THE INVENTION

The conventional approach for obtaining accurate quantitative measurements of analyte concentration requires the use of equipment intensive analysis. This approach for determining the concentration of an analyte in a solution requires the use of expensive equipment using spectroscopy, chromatography, NMR, atomic absorption or other analytical procedures that can also be difficult and time consuming to use. Also, a relatively large volume of the solution may be required for the tests.

The use of paper-based microfluidic systems for use in a variety of applications including chemical analysis was first proposed in Martinez, A. W.; Phillips, S. T.; Butte, M.; Whitesides, G. M., Patterned Paper as a Platform for Inexpensive, Low-volume, Portable Bioassays, Angew. Chem. Int. Ed., 2007, 46, 1318-1320. The advantages of using such systems are their low cost and portability. Furthermore, the sample volume amount can be significantly reduced which is helpful when the obtained sample amount is limited (example a biological sample from a hospital patient). It should be noted that the term "paper" is used in the application to refer to cellulosic material including woven fabrics and non-woven material in addition to paper.

Further developments of such paper-based microfluidic systems are described in the applicant's Australian provisional patent application nos. 2008903553 and 2008905776. In the applicant's microfluidic systems, a hydrophobic/hydrophilic contrast is provided on the surface of the paper substrate to thereby define microfluidic channels for controlling the transport of aqueous solutions due to capillary action without the need of external pumping.

The concentration of a test sample may be determined by using colourmetric methods with such microfluidic systems by reacting the test sample with an indicator solution. The accuracy of the results are however influenced by many external factors including environmental conditions such as the ambient temperature and relative humidity, the quality and age of the paper, the quality and the settings of the scanner or camera used to record the results, or the means to transmit the results electronically. This can lead to significant errors in the colorimetric analytical results. Therefore, the same test sample measured using different paper substrates, using different scanners or cameras, or transmitted using different electronic transmission systems with different software could result in significant variations in the result.

The same principle can be used with ELISA-type of analysis based on paper, where bioconjugates are fixed on paper.

SUMMARY OF THE INVENTION

It is therefore an object of the present invention to more accurately determine the concentration of a test sample using paper-based microfluidic systems.

With this in mind, there is provided a method of determining the concentration of a test fluid sample using a paper-based microfluidic system having a plurality of hydrophilic testing zones, including:

a) depositing said test fluid sample on at least one said testing zone;

b) depositing a plurality of standard fluid samples or reactives of differing known concentrations on other said testing zones;

c) introducing an indicator solution to each said test zone to thereby react with the deposited fluid sample and result in a colour intensity change which is a function of the fluid sample concentration; and d) comparing the differences in colour intensity between the test fluid sample and the standard fluid samples or reactives to thereby determine the concentration of said test fluid sample.

The deposition of the standard fluid samples or reactives can be done prior to or during the deposition of the test sample.

The use of a plurality of standard fluid samples or reactives of different known concentrations provides an internal self-calibration for the method according to the present invention. This can lead to more accurate results being obtained not withstanding the various external factors that refer to previously. This is because the test results are determined on the basis of the relative differences between the test fluid sample and the standard fluid samples or reactives, thereby avoiding the influences associated with the external factors referred to previously.

The results may therefore be recorded using a variety of equipment including a desktop scanner or even a phone camera. The image may therefore be imported into a graphics program such as Adobe Photoshop®, and converted into greyscale mode. The main colour intensities can then be modified using the histogram function of the software. The ultimate mean intensity value of each test zone may preferably then be obtained by subtracting the measured average intensity from the mean intensity of a blank control zone and converted as a graph to obtain a calibration curve, the graph plotting mean intensity against solution concentration.

ELISA is an enzyme-linked immunosorbent assay. Paper-based microfluidic device may be designed to perform ELISA-like assay. In this assay certain amounts of antigen are fixed on the paper surface, a specific antibody is applied over the paper surface so that it can bind to the antigen. This antibody is bonded to an enzyme. In the last step of ELISA a substance is added to convert the enzyme to some detectable signal.

There is also provided a system for determining the concentration of a test fluid sample, said system including:

a) a paper-based microfluidic system having a plurality of hydrophilic testing zones, said test fluid sample being depositable on at least one testing zone;

b) a plurality of standard fluid samples or reactives of differing known concentration for depositing on other said testing zones;

c) an indicator solution for introducing to each test zone to thereby react with the fluid samples and result in a colour intensity change which is a function of the fluid sample concentration, wherein by comparing differences in colour intensity between the test fluid sample and the standard fluid samples or reactives the concentration of the test fluid sample can be determined.

BRIEF DESCRIPTION OF THE DRAWINGS

It will be convenient to further describe the invention with respect to the accompanying drawings which illustrate the method according to the present invention. Other embodiments of the invention are possible, and consequently, the particularity of the accompanying drawings is not to be understood as superseding the description of the invention.

In the drawings.

DETAILED DESCRIPTION OF THE INVENTION

Figure 1:
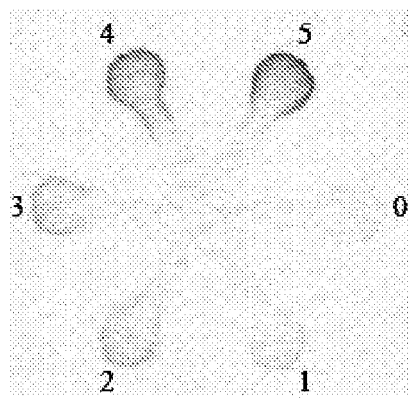
FIG. 1 shows a paper-based microfluidic system for creating an $NO_2^-$ calibration curve according to the present invention.

The invention will now be described with reference to the following examples describing different possible utilisations of the present invention. It is however to be appreciated that the invention does not restrict to these examples.

The fabrications of the paper-based microfluidic systems were achieved using the techniques as described in the applicant's above noted provisional applications.

Whatman filter paper (No. 4) was selected as the substrate to prepare the microfluidic systems. Two methods were used for fabrication—plasma treatment and ink jet printing. The former patterning method was based on the principle of using a vacuum plasma reactor (K1050X plasma asher (Quorum Emitech, UK)) and premade masks to selectively dehydrophobize filter paper samples which have already been hydrophobized by alkyl ketene dimer (Wax 88 konz, BASF) beforehand. The latter one was using a commercial desktop ink jet printer to selectively deposit alkenyl ketene dimer (Precis 900, Hercules Australia Pty Ltd) onto filter paper. The microfluidic systems, were fabricated with a pattern consisting of six detection zones and one central inlet zone.

Millipore-purified water was used to prepare all liquid samples required for testing the performance of microfluidic systems. Serially diluted nitrite and uric acid standard solutions were prepared with sodium nitrite (≥99%, Sigma-Aldrich) dissolved in water and uric acid (≥99%, Sigma-Aldrich) dissolved in sodium hydroxide solution (0.2 mol/L), respectively.

The indicator solution for $NO_2^-$ contains 50 mmol/L sulfanilamide (≥99%, Sigma-Aldrich), 330 mmol/L, citric acid (≥99.5%, Sigma-Aldrich), and 10 mmol/L N-(1-naphthyl) ethylenediamine, ≥98%, Sigma-Aldrich).

The indicator solution for UA consists of the 1:1 mixture of solution A (2.56% (w/v) 2,2'-biquinoline-4,4'-dicarboxylic acid disodium salt hydrate, ≥98%, Sigma-Aldrich) and solution B (20 mmol/L sodium citrate and 0.08% (w/v) copper (II) sulfate, ≥99%, Sigma-Aldrich).

For creating a nitrite calibration curve, one blank control (water, 0.5 μL) and five serially diluted nitrite standard solution samples (with concentration ranging from 78 μmol/L to 1250 μmol/L, 0.5 μL) were deposited onto six detection zones in sequence using the eppendorf Research® pipette (0.1-2.5 μL).

A nitrite solution (500 μmol/L $NO_2^-$) was assumed as the sample solution of unknown concentration. This sample solution (0.5 μL) was spotted onto one detection zone with serially diluted nitrite standard solution samples (156 μmol/L to 2500 μmol/L, 0.5 μL) on the other detection zones in sequence. In this assay, water (0.5 μL) was added onto the central inlet zone as the blank control.

For uric acid assay, a uric acid solution (500 μmol/L UA) was assumed as unknown sample solution and successively loaded with five serially diluted UA standard solution samples (100 μmol/L to 1600 μmol/L) onto each detection zone of the μPAD. NaOH solution (0.2 mol/L) was used as the blank control in this assay.

In all the above assays, corresponding indicator solutions (5 μL) were introduced into detection zones from the inlet zone with the eppendorf Research® pipette (0.5-10 μL) owing to the capillary penetration. For each assay, six independent measurements have been taken with six devices.

The results of the colorimetric assays were imaged with a desktop scanner (Epson Perfection 2450, color photo setting, 1200 dpi resolution), then imported into Adobe Photoshop® and converted into grayscale mode. The mean color intensities were quantified using the histogram function of Adobe Photoshop®. The ultimate mean intensity value of each detection zone was obtained by subtracting the measured average intensity from the mean intensity of blank control and transferred to Microsoft Excel® to obtain calibration curve data.

Example 1

Figure 2:
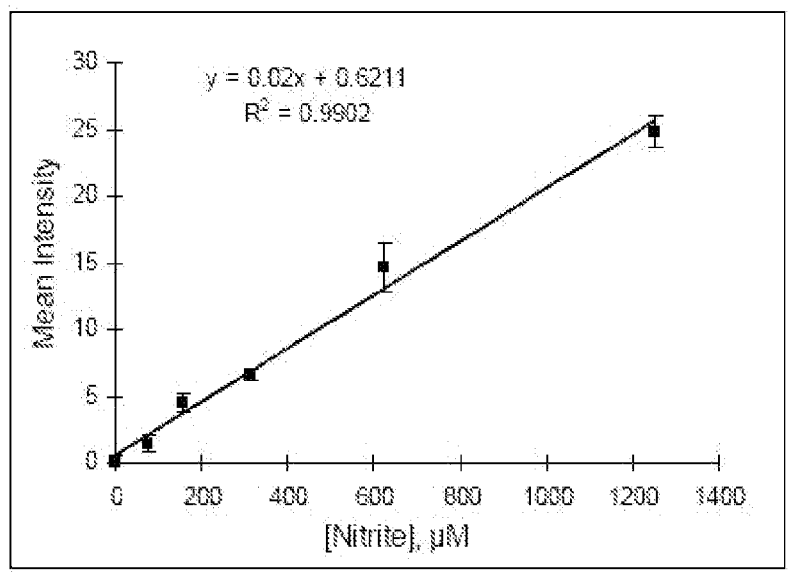
FIG. 2 shows an $NO_2^-$ calibration curve obtained from the test results from the microfluidic system as shown in FIG. 1.

In this example, an $NO_2^-$ calibration curve was created as shown in FIGS. 1 and 2. The colorimetric testing of $NO_2^-$ was based on the principle of the Griess reaction which is a common quantification measurement method for $NO_2^-$. In this assay, serially diluted $NO_2^-$ standard solutions (78, 156, 312, 625, 1250 μmol/L) were deposited into each detection zone 1-5 in sequence, while the blank control solution was spotted on the detection zone 0. Then the indicator solution for $NO_2^-$ was introduced into the device via inlet zone. When the indictor solution penetrated into testing zones by capillary action and contacted with the analyte, the citric acid within the indicator solution converted $NO_2^-$ to H $NO_2^-$. The nitrous acid then transformed sulfanilamide into diazotized sulfanilamide which coupled with N-(1-napthyl)-ethylenediamine to form a pink azo compound. The resulting color developed in each detection zone changes from almost colorless (zone 0) to pink (zone 5) due to the different concentration of standard solution samples (FIG. 1). In FIG. 2, the value of mean color intensity of each standard sample is the average of six independent measurements which were taken using six microfluidic systems, measured and calculated with software. The error bar is the relative standard deviation.

Linear least-squares fitting of the nitrite data gave coefficient of determination ($R_2$) of 0.9902. The mean color intensity is proportional to the $NO_2^-$ concentration. This assay certified that we can use paper-based microfluidic systems (six-channel pattern as an example) to create calibration curves for quantitative analysis.

Example 2

Figure 3:
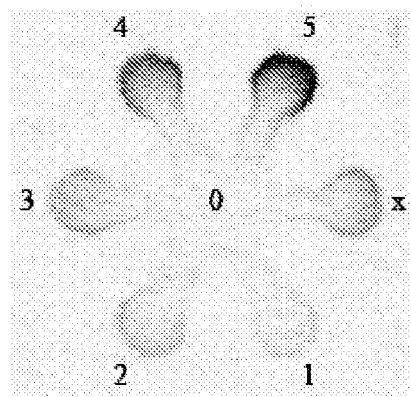
FIG. 3 shows a paper-based microfluidic system for determining the $NO_2^-$ concentration of an unknown sample according to the present invention.
Figure 4:
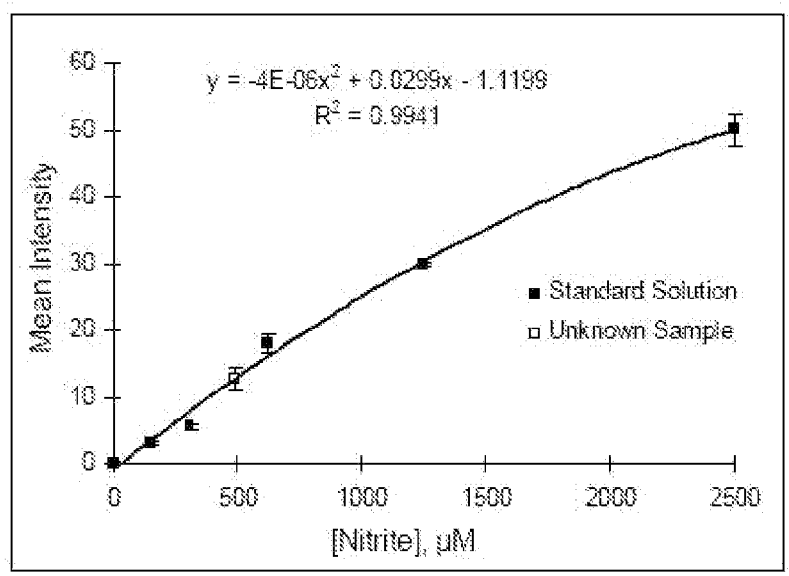
FIG. 4 shows a calibration curve obtained from the test results from the microfluidic system as shown in FIG. 3.

In this example, the $NO_2^-$ concentration of an unknown sample was measured. To measure the nitrite concentration of an unknown sample using paper-based microfluidic systems, we prepared a blank control solution (0 μmol/L $NO_2^-$, deposited on zone 0), five standard solutions (156, 312, 625, 1250, 2500 μmol/L $NO_2^-$, deposited on zone 1-5), and a 500 μmol/L $NO_2^-$ solution (deposited on zone x) as an assumed unknown sample solution. The indicator solution was still introduced into the system from central inlet zone which developed different color in different testing zones (FIG. 3). In this assay, six microfluidic systems were used to run six independent tests which provided the mean color intensity and error bar for every standard solution to create the calibration curve (FIG. 4) which gave a quadratic regression equation for calculating the unknown sample concentration. As long as the measured concentration is close to the real value, the paper-based microfluidic systems are deemed to be efficient tools to quantitatively analyze the analyte concentration of an unknown sample solution. The result obtained from software analyses showed that the measured average color intensity for the unknown sample is 12.684, thus the $NO_2^-$ concentration of unknown sample from calculation is 507 μmol/L (1.4% relative error compared with the real concentration of 500 μmol/L).

Example 3

Figure 5:
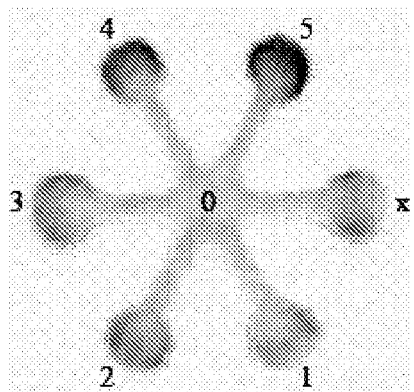
FIG. 5 shows a paper-based microfluidic system for measuring the Uric Acid (UA) concentration of an unknown sample according to the present invention.
Figure 6:
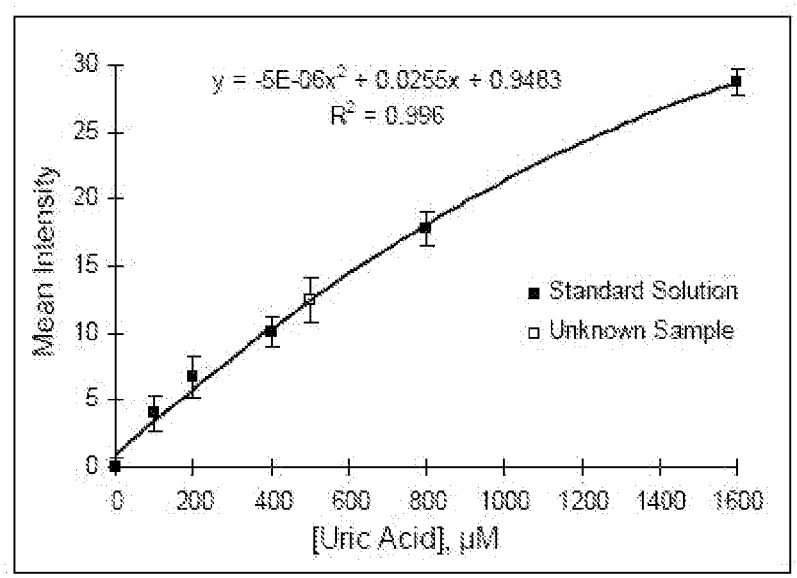
FIG. 6 shows a calibration curve obtained from the test results from the microfluidic system as shown in FIG. 5.

In this example, the UA concentration of an unknown sample was measured as shown in FIGS. 5 and 6.

The colorimetric assay of uric acid was based on a bicinchoninate chelate method. When the indicator solution for UA came into the detection zone, Cu (II) in the indicator solution was reduce to Cu (I) by UA which has been loaded on the testing zone beforehand, then the cuprous ion formed a purple chelate product with sodium bicinchoninate. The resulting color developed in testing zones 0-5 gradually became darker from light purple to purple corresponding to different UA concentrations (0, 100, 200, 400, 800, 1600 μmol/L) (FIG. 6). The data and error bars in FIG. 7 are the mean and relative standard deviation, respectively, from 6 independent measurements taken using six devices. We prepared the sample solution with 500 μmol/L uric acid and assumed this solution as the unknown sample which was also deposited on the testing zone x. With software analyses, the average of six measured values of color intensity is 12.492 for unknown sample; hence the mean UA concentration of six unknown samples can be calculated from the regression equation, which was 502 μmol/L. The relative error is 0.4% compared with the real concentration value (500 μmol/L).

The result from all assays illustrated that the paper-based microfluidic systems are sufficient to operate parallel tests on different detection zones simultaneously. The amount of tests ran with one system correlates with the number of testing zones which is changeable according to different predesigned patterns. In the described examples, the six-channel pattern is capable of detecting up to seven samples at one time, thereby creating a calibration curve and providing a regression equation for unknown sample concentration measurement. This method is a low-cost, rapid and simple concentration detection method by virtue of colorimetric chemistry of the tested analyte.

Microfluidic paper-based multifluidic systems, combined with the colorimetric reaction of analyte and the existing computer software (e.g. Adobe Photoshop®), can provide a cheap and easy-to-use tool for the quantitative detection of unknown sample concentration. The raw material for these microfluidic systems—paper—is relatively economical and the fabrication method of these systems is quite simple. Therefore, the paper-based microfluidic system can be a useful tool when measurements performed in less-industrialized area or remote region with limited resources. Moreover, this method substantially reduces the sample volume, which is helpful when the obtainable sample amount is limited (e.g. the biological sample from patients).

The invention claimed is:

1. A method of determining the concentration of a test fluid sample using a paper-based microfluidic system having a plurality of hydrophilic testing zones in fluid communication with and distributed radially from a central inlet zone each zone being patterned onto a paper substrate, the method comprising:
   a) depositing said test fluid sample directly onto at least one said testing zone;
   b) depositing a plurality of standard fluid samples or reactives of differing known concentrations directly onto other said testing zones;
   c) introducing an indicator solution to the central inlet zone, the indicator solution penetrating into each said testing zone to thereby react with each of the deposited test and standard fluid samples and result in a colour intensity change which is a function of the test and standard fluid sample concentrations; and
   d) comparing the differences in colour intensity between the test fluid sample and the standard fluid samples or reactives to thereby determine the concentration of said test fluid sample.

2. The method according to claim 1 further comprising quantifying the colour intensity in each said testing zone as a function of the known standard fluid sample concentrations to thereby produce a calibration curve from which the concentration of the test fluid sample can be obtained.

3. The method according to claim 1, wherein one said testing zone is deposited with water or a standard solution to provide a blank control zone.

4. The method according to claim 1, wherein the standard fluid samples or reactives are deposited prior to the deposition of the test fluid sample.

5. The method according to claim 1, wherein enzyme-linked immunosorbent assay (ELISA) is performed using bioconjugation.

6. A method of determining the concentration of a test fluid sample using a paper-based microfluidic system having a plurality of hydrophilic testing zones in fluid communication with and surrounding a central inlet zone, each zone being patterned onto a paper substrate, the method comprising:
   a) depositing said test fluid sample directly onto at least one said testing zone;
   b) depositing a plurality of standard fluid samples or reactives of differing known concentrations directly onto other said testing zones;
   c) introducing an indicator solution to the central inlet zone, the indicator solution penetrating into each said testing zone to thereby react with each of the deposited test and standard fluid samples and result in a colour intensity change which is a function of the test and standard fluid sample concentrations; and d) comparing the differences in colour intensity between the test fluid sample and the standard fluid samples or reactives to thereby determine the concentration of said test fluid sample.

7. The method according to claim 1, wherein the plurality of hydrophilic testing zones are equidistant from the central inlet zone.

* * * * *